United States Patent [19]

Levin

[11] Patent Number: 6,013,460
[45] Date of Patent: Jan. 11, 2000

[54] MODIFIED WESTERN BLOT MEMBRANE AND METHOD FOR DETECTING LYME DISEASE AND OTHER TICK-BORNE DISEASES

[75] Inventor: Andrew E. Levin, Wellesley, Mass.

[73] Assignee: Immunetics, Incorporated, Cambridge, Mass.

[21] Appl. No.: 08/928,907

[22] Filed: Sep. 12, 1997

[51] Int. Cl.$^7$ ..................................................... G01N 33/53
[52] U.S. Cl. ........................... 435/7.1; 435/7.32; 435/7.9; 435/7.92; 435/975; 436/514; 436/516; 436/518; 436/530
[58] Field of Search ................................ 435/5, 7.1, 7.32, 435/7.9, 7.92, 974, 975; 436/518, 530, 514–516

[56] References Cited

U.S. PATENT DOCUMENTS

| | | |
|---|---|---|
| 4,859,419 | 8/1989 | Marks et al. . |
| 4,888,276 | 12/1989 | Shelburne . |
| 5,100,626 | 3/1992 | Levin . |
| 5,155,022 | 10/1992 | Naqui . |
| 5,187,065 | 2/1993 | Schutzer . |
| 5,217,872 | 6/1993 | Dorward . |
| 5,308,753 | 5/1994 | Dorward . |
| 5,324,630 | 6/1994 | LeFebvre . |
| 5,470,712 | 11/1995 | Simpson . |
| 5,494,797 | 2/1996 | McCann . |
| 5,620,862 | 4/1997 | Padula ..................................... 435/7.32 |
| 5,656,451 | 8/1997 | Flavell et al. . |

OTHER PUBLICATIONS

"Recommendation for Test Performance and Interpretation from the Second National Conference on Serologic Diagnosis of Lyme Disease," MMWR MORB MORTAL WKLY REP., vol. 44, No. 31, pp. 590–591, XP002088879 (Aug. 11, 1995).

Dumler, J., et al., "A Population–Based Seroepidemiologic Study of Human Granulocytic Ehrlichiosis and Lyme Borreliosis on the West Coast of Sweden," J. of Infectious Diseases, vol. 175, No. 3, pp. 720–722 (1997).

Magnarelli, L., et al., "Coexistence of Antibodies to Tick–Borne Pathogens of Babesiosis, Ehrlichiosis, and Lyme Borreliosis in Human Sera," J. Clinical Microbiology, vol. 33, No. 11, pp. 3054–3057 (Nov. 1995).

Brouqui et al. "Serologic Diagnosis of Human Monocytic Ehrlichiosis by Immunoblot Analysis", CLINICAL AND DIAGNOSTIC LABORATORY IMMUNOLOGY, vol. 1, No. 6 (Nov. 1994), pp. 645–649. ABSTRACT ONLY.

Benach, J.L. et al., "Serological Evidence for Simultaneous Occurrences of Lyme Disease and Babesiosis," J. Infect. Dis . 152:473–477 (1985).

Boustani, M.R. et al., "Acute Respiratory Failure in Patients Treated for Babesiosis," Am. J. Respir. Crit. Care. Med . 149:1689–1691 (1994).

Cahill, K.M., "Babesiosis: Unappreciated Even in Endemic Areas," J. Comm. Health 20(4):315–320 (1995).

Chisholm, E.S. et al., "Indirect Immunofluorescence Test for Human Babesia Microti Infection: Antigenic Specificity," Am. J. Trop. Med. Hyg . 35:921–925 (1986).

Chisholm, E.S. et al., "Babesia Microtia Infection in Man: Evaluation on an Indirect Immunofluorescent Antibody Test," Am. J. Trop. Med. Hyg . 27:14–19 (1978).

Garcia, L.S. et al., Diagnostic Medical Parasitology , Washington, D.C., p. 131–135 (Second Edition, 1993).

(List continued on next page.)

Primary Examiner—Jeffrey Stucker
Attorney, Agent, or Firm—Foley, Hoag & Eliot, LLP

[57] ABSTRACT

Modified Western blot membranes and methods of using same are provided which allow confirmation of Lyme disease and screening for at least one additional tick-borne disease. The membranes and methods of the present invention may thus be used to screen for the presence of tick-borne diseases which may be transferred along with Lyme disease. A Western blot assay may also be employed to confirm the presence of such additional tick-borne disease.

16 Claims, 1 Drawing Sheet

OTHER PUBLICATIONS

Herwaldt, B.L. et al., "Babesiosis in Wisconsin: A potentially Fatal Disease," *Am. J. Trop. Med. Hyg* . 53(2):146–151 (1995).

Horowitz, M.L. et al., "Delayed Onset Adult Respiratory Distress Syndrome in Babesiosis," *Chest* 106(4):1299–1301 (1994).

Krause, P.J. et al., "Efficacy of Immunoglobulin M Serodiagnostic Test for Rapid Diagnosis of Acute Babesiosis," *J. Clin. Microbiol* . 34:2014–2016 (1996).

Krause, P.J. et al., "Babesiosis: An Underdiagnosed Disease of Children," *Pediatrics* 89:1045–1048 (1992).

Krause, P.J. et al., "Diagnosis of babesiosis: Evaluation of a Serologic Test for the Detection of *Babesia microti* Antibody," *J. Infect. Dis* . 169:923–926 (1994).

Machtinger, L. et al., "Treatment of Babesiosis by Red Blood Cell Exchange in an HIV–Positive, Splenectomized Patient," *J. Clin. Apheresis* 8:78–81 (1993).

Marcus, L.C. et al., "Fatal Pancarditis in a Patient with Coexistent Lyme Disease and Babesiosis. Demonstration of Spirochetes in the Myocardium." *Ann. Intern. Med* . 103:374–376 (1985).

Mitchell, P.D. et al., "Immunoserologic Evidence of Coinfection with *Borrelia burgdorferi, Babesia microti* , and Human Granulocytic Ehrlichia Species in Residents of Wisconsin and Minnesota," *J. Clin. Microbiol* . 34:724–727 (1996).

Patarroyo, J.H. et al., "Exoantigens of an Attenuated Strain of *Babesia bovis* Used as a Vaccine Against Bovine Babesiosis," *Vet. Parasitol* . 59:189–199 (1995).

Persing, D.H. et al., "Detection of *Babesia microti* by Polymerase Chain Reaction," *J. Clin. Micro* . 30:2097–2103 (1992).

Piesman, J. et al., "Simultaneous Transmission of *Borrelia burgdorferi* and *Babesia microti* by Individual Nymphal *Ixodes dammini* Ticks," *J. Clin. Micro* 25:2012–2013 (1987).

Popovsky, M.A. et al., "Prevalence of Babesia Antibody in a Selected Blood Donor Population," *Transfusion* 28:59–61 (1988).

Quick, R.E. et al., "Babesiosus in Washington State: A New Species of Babesia?" *Annals of Int. Med* . 119:284–290 (1993).

Rosenbaum, G.S. et al., "Atypical Lymphocytosis in Babesiosis, " *Clin. Infect. Dis* . 20:203–204 (1995).

Ruebush, T.K. II et al., "Human Babesiosis on Nantucket Island," *N. Eng. Med* . 297(15):825–827 (1977).

Towbin, H. et al., "Electrophoretic Transfer of Proteins from Polyacrylamide Gels to Nitrocellulose Sheets: Procedure and Some Applications," *PNAS (USA)* 76:4350–4354 (1979).

MODIFIED WESTERN BLOT MEMBRANE AND METHOD FOR DETECTING LYME DISEASE AND OTHER TICK-BORNE DISEASES

FIELD OF THE INVENTION

The present invention relates generally to a diagnostic method for detecting tick-borne disease and more specifically, a modified Western blot membrane and method of using same for detecting Lyme disease as well as other tick-borne diseases which may accompany Lyme disease during its transmission. In particular, the modified Western blot membrane and method of the present invention may be used to simultaneously confirm Lyme disease and screen for at least one additional tick-borne disease.

BACKGROUND OF THE INVENTION

Lyme disease is a progressive, systemic infection caused by the spirochete *Borrelia burgdorferi*. The disease is transmitted to man by the bite of the deer tick (*Ixodes scapularis* and other species). Diagnostic tests for Lyme disease rely mainly on the detection of human antibodies to spirochetal antigens. The principal test used for screening human sera for antibodies to the Lyme spirochete is enzyme-linked immunosorbent assay (ELISA). Due to the significant inaccuracies inherent in ELISA, sera which are ELISA-positive or indeterminate are often subjected to a confirmatory test. The confirmatory test now in most common use and officially recommended by the U.S. Centers for Disease Control (CDC) is the Western blot. In a conventional Western blot assay, antigens of a given pathogen are resolved into discrete bands on the surface of a paper-like nitrocellulose membrane. The serum to be tested is allowed to react with the antigen bands, and serum antibodies which bind specific bands are detected with a labeled anti-human antibody reagent. Typically, results of the Western blot test appear as a series of bands on a membrane strip. The pattern of bands is compared with the band pattern of known positive sera to produce a diagnostic result. The exact position of bands, and the number of bands which correlate with positivity, differ depending on the pathogen.

Considerable effort has been expended to develop new and improved diagnostic tests for Lyme disease. For example, U.S. Pat. No. 5,187,065 discloses methods of detecting Lyme disease in mammals that otherwise show seronegativity due to the generation of immune complexes which "hide" the antibodies raised to the spirochete; disassociation of such complexes followed by immunological assay procedures such as ELISA are described. U.S. Pat. No. 5,470,712 provides bioassays which incorporate non-flaggellar *B. burgdorferi* proteins, or antibodies raised to such proteins, to create an assay where such proteins or antibodies are bound to a surface and form complexes with certain components of the serum. Similarly, U.S. Pat. No. 5,308,753 teaches the formation of assays which may be used to diagnose Lyme and other diseases which induce primary or secondary IgM antibody-mediated immunity. U.S. Pat. No. 5,217,872 teaches a method of detecting *B. burgdorferi* antigens through an assay which utilizes vesicle proteins released from the spirochete, while U.S. Pat. Nos. 5,494,797 and 5,324,630 teach the detection of the Lyme spirochete via oligonucleotide probes. U.S. Pat. No. 4,888,276 describes a reliable, noninvasive method for detecting antigens of *B. burgdorferi* from the urine of affected individuals and U.S. Pat. No. 5,155,022 teaches an improved method of assaying for Lyme disease by eliminating cross-reacting antibodies. Both U.S. Pat. Nos. 4,859,419 and 5,100,626 provide apparati that are able to assay multiple samples for a specific disease such as Lyme. However, none of these patents teach a method of simultaneously assaying for Lyme disease and other diseases.

The same ticks which transmit Lyme disease to humans also transmit babesiosis, an underdiagnosed parasitic infection which may have serious consequences. In the United States, the major pathogen is the protozoan *Babesia microti*; in Europe and other countries, other species of Babesia including *B. divergens, B. bovis* and *B. bigemina,* all known pathogens of cattle, have been implicated. Despommier, D. et al., *Parasitic Diseases,* Springer-Verlag, New York (1995). Ehrlichiosis, caused by either of two rickettsial Ehrlichia species, is another disease which the Ixodid tick may transmit. In addition, a babesiosis-like illness in the northwestern United States has been attributed to an unidentified Babesia-like organism, thus far termed WA1. Quick, R. et al., *Annals of Int. Med.* 119: 284–290 (1993).

The clinical symptoms and severity of babesiosis cover a wide spectrum. While the disease is subclinical in most cases, it may be severe to fatal in others. Telford, S. R. III et al., *Topley and Wilson's Microbiology,* in press; Herwaldt, B. L. et al., *Am. J. Trop. Med. Hyg.* 53(2): 146–151; Garcia, L. S. et al., *Diagnostic Medical Parasitology,* Washington, D.C., p. 131–135 (Second Edition, 1993); Boustani, M. R. et al., *Am. J. Respir. Crit. Care. Med.* 149: 1689–1691 (1994); Horowitz, M. et al., *Chest* 106(4): 1299–1301 (1994); Rosenbaum, G. S. et al., *Clin. Infect. Dis.* 20: 203–204 (1995); Machtinger, L. et al., *J. Clin. Apheresis* 8: 78–81 (1993). Splenectomy, immunosuppression, and advanced age are significant prognostic indicators. Early symptoms may appear within one to several weeks post-infection, and typically include malaise, anorexia, and fatigue. In susceptible individuals, these progress quickly to more serious symptoms, including fever up to 40° C., sweating, myalgia, nausea, vomiting, headache, shaking chills, emotional lability and depression, hemoglobinuria, hyperesthesia, and pulmonary edema. Blood analyses may reveal anemia, thrombocytopenia, and low white blood cell count, while lactic dehydrogenase, bilirubin and transaminases may appear at elevated levels. The wide range in symptoms makes the clinical diagnosis of babesiosis difficult, and additionally so in view of the possibility of either confusion or coinfection with Lyme disease and/or ehrlichiosis.

Co-infected patients may be subject to more severe illness than caused by either pathogen alone. Significant frequencies of co-infection have been reported in areas endemic for babesiosis and Lyme disease. Mitchell, P. D. et al., *J. Clin. Microbiol.* 34: 724–727 (1996). Both diseases appear to be rising in incidence, perhaps due to changes both in public awareness of tick-borne diseases and in the interactions of man and the surrounding natural environment. Because therapeutic treatment and prognosis differ for the various diseases, accurate diagnosis is essential for successful clinical management of the patient.

Babesia infects and multiplies within the erythrocytes of the host and thus laboratory testing for babesiosis has traditionally been based on examination of Giemsa-stained blood smears. Telford, S. R. III et al., *Topley and Wilson's Microbiology,* in press; *Diagnostic Medical Parasitology,* Washington, D.C., p. 131–135 (Second Edition, 1993). Babesia may be visualized in parasitized erythrocytes as pear-shaped piroplasms (hence the common name for babesiosis, "piroplasmosis") or rings, and infrequently as tetrads (maltese cross forms) which are considered as definitive evidence of infection. Parasitemia in infected individuals may vary between 1–20%, while in splenectomized patients, it may attain 85%. Nevertheless, low level parasitemia is common enough so that failure to observe the parasite in blood smears does not prove the absence of infection with Babesia. Babesia may also be revealed by inoculation of patient blood samples into hamsters, which develop high levels of parasitemia; however, this technique may require up to 6 weeks to yield detectable results.

Serology provides a useful diagnostic approach for babesiosis. Telford, S. R. III et al., *Topley and Wilson's Microbiology,* in press; *Diagnostic Medical Parasitology,* Washington, D.C., p. 131–135 (Second Edition, 1993). IgM and IgG antibodies to Babesia are produced by infected individuals, and may be detected where direct visual evidence of parasitemia is lacking. An indirect immunofluorescence assay has been developed and has been applied as a diagnostic method. Krause, P. J. et al., *J Infect. Dis.* 169: 923–926 (1994); Chisholm, E. S. et al., *Am. J. Trop. Med. Hyg.* 27: 14–19 (1978); Chisholm, E. S. et al., *Am. J. Trop. Med. Hyg.* 35: 921–925 (1986). Immunofluorescence testing of babesiosis patient sera has shown very little crossreactivity between *B. microti* and the WA1 stain found in some Washington State patients. Telford, S. R. III et al., *Topley and Wilson's Microbiology,* in press; Quick, R. E. et al., *Ann Intern. Med.* 119(4): 284–290 (1993).

In another diagnostic method, Babesia DNA is detected by polymerase chain reaction (PCR). Persing, S. et al., *BioTechniques* 17: 788–791 (1994). While the sensitivity of PCR is one of its main advantages, PCR at present remains a technique beyond the expertise of the average diagnostic laboratory. In inexperienced hands, PCR may lead to an inaccurate diagnosis. Thus, while it would be preferable to utilize a rapid and accurate screening method for diagnosing Babesiosis, especially one which could be run simultaneously with tests for Lyme and other diseases, none have thus been developed.

It would thus be desirable to provide a method for detecting Lyme disease as well as at least one additional disease. It would further be desirable that such a method combine the confirmatory Western blot detection of Lyme disease with a screening test for diseases which may accompany Lyme disease during its transmission. It would also be desirable that such a method be able to screen for diseases such as babesiosis and ehrlichiosis. It would further be desirable that such a method have the capability of being automated. It would additionally be desirable to provide a method wherein initial screening is followed with a confirmatory test. It would further be desirable to provide a method wherein the confirmatory test is a Western blot assay.

SUMMARY OF THE INVENTION

Modified Western blot membranes and methods of using same are provided which allow confirmation of Lyme disease and detection of at least one additional tick-borne disease. The membrane of the present invention provides a confirmatory Western blot assay for Lyme disease in combination with a "dot-blot" screening assay for diseases which may be transmitted along with Lyme disease. By combining the confirmatory Western blot assay for Lyme disease with the dot-blot screening assay for other diseases, the presence of more than one disease transmitted by the Lyme spirochete such as babesiosis and ehrlichiosis, may be detected. Moreover, a Western blot assay for the additional tick-borne disease may be performed to confirm the presence of antibody to the additional tick-borne disease.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

DETAILED DESCRIPTION OF THE PREFERRED EMBODIMENTS

Figure 1A:
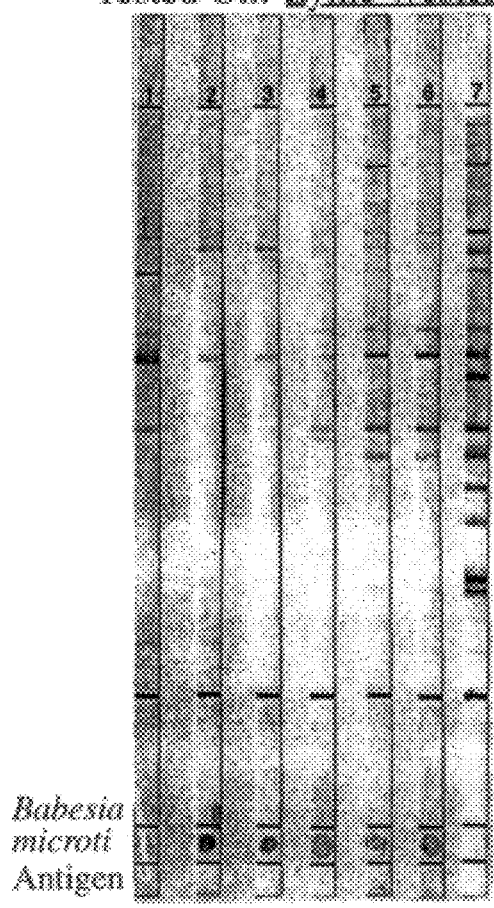
FIG. 1A shows the *Babesia microti* antigen dot on Lyme Western blot strips which permits screening for babesiosis.

Modified Western blot membranes and methods for confirming the presence of Lyme disease while screening for at least one additional tick-borne disease are provided. In a preferred embodiment, the membrane of the present invention is a Western blot for Lyme disease in combination with a "dot-blot" for detecting the presence of at least one additional tick-borne disease. By utilizing the membrane and method of the present invention, a sample may be simultaneously tested for Lyme disease and screened for the presence of other tick-borne diseases such as babesiosis and ehrlichiosis. In addition, a follow-up Western blot assay may be performed to confirm the presence of the other tick-borne disease.

The Western blot is an accurate method of assaying for the presence of a particular protein within a biological sample. The general methodology of the Western blot is comprised of applying the sample to a polyacrylamide gel and separating the proteins through the technique of gel electrophoresis. The proteins, which have been separated into discrete bands, are subsequently transferred to a sheet (e.g., nitrocellulose) by way of a blotting chamber. Once the protein bands have been transferred, the blot is treated with antibody specific to the particular antigen of interest; if the antigen is present, the antibody will bind to the antigen. Free antibody is washed away, the blot is treated with a second antibody which is capable of binding to a site on the first antibody, and the blot is rinsed again to remove excess antibody. In order to detect binding, the second antibody may carry a radiolabel or may be linked to an enzyme as in the ELISA technique. The enzyme linked to the antibody may then in turn react with a substrate applied to the blot which, for example, generates a colored product. In the case of a radiolabel, the bands may be visualized through the technique of autoradiography, where the radioactive blot is exposed to photographic film for a time sufficient to visualize the protein band or bands of interest. The presence of very small quantities of antigen may thus be detected due to the highly sensitive nature of the Western blotting technique, and hence its value as a confirmatory test.

The dot blot test of the present invention which is combined on a membrane with the Western blot of the present invention, is similar in principle to conventional ELISA, with the exception that a membrane is substituted for the plastic microplate, and antigen is applied to the membrane as a dot. The method generally comprises applying antibody, which is specific to the antigen of interest, directly to a membrane. The membrane is then washed to remove unbound antibody. The sample containing the antigen of interest is then applied to the membrane, and the antigen subsequently binds to the antibody attached to the membrane. The membrane is again washed to remove unbound molecules, treated with a second antibody specific to a different site on the antigen of interest, and washed to remove unbound enzyme conjugate. This antibody is linked to an enzyme, such as alkaline phosphatase, which reacts with an applied substrate to yield a colored product from a colorless one, or by converting a nonfluorescent substrate into a fluorescent one. Because the test is membrane-based like the Western blot, the presence of antibody is indicated by deposition of a colored, insoluble reaction product to the membrane. The results appear as a dot, rather than bands as in the Western blot, since antigen is applied to the membrane in a single drop rather than as electrophoretically resolved bands of protein. As the dot blot is based on unfractionated antigen and does not provide the means to distinguish between antibody reactions with antigen fractions which are either more or less specific to a given pathogen, the dot biot test is generally used as a screening rather than a confirmatory test. In a preferred embodiment, the preliminary screening portion of the method of the present invention is followed by a more sensitive Western blot assay to confirm the screening test.

In one embodiment of the present invention, a dot blot screening test for Babesia is combined with a Western blot confirmatory test for Lyme disease by applying a dot of Babesia antigen to one end of a membrane, preferably a nitrocellulose membrane, prepared as a Lyme Western blot membrane (FIG. 1A). Thus, resolved Lyme antigen bands cover the upper portion of the membrane and permit it to be used as a conventional Lyme Western blot. For convenience, the dot of Babesia microti antigen was applied below the lowermost Lyme antigen band, and is therefore clearly distinguishable from the Lyme bands. However, it will be appreciated that the dot may be placed anywhere on the membrane. The membrane is processed with a serum sample in the same manner as a conventional Lyme Western blot membrane as known to those skilled in the art. In a preferred embodiment, the following steps are performed: 1) incubation of the membrane with diluted serum; 2) buffer wash to remove unbound antibody; 3) incubation with enzyme-conjugated anti-immunoglobulin; 4) buffer wash to remove unbound enzyme conjugate; and 5) incubation with enzyme substrate. If the serum sample contains antibodies to both *Borrelia burgdorferi* and *Babesia microti,* then bands will appear on the Western blot portion of the membrane and a dot will appear on the end of the membrane below the bands (FIG. 1A). If the serum sample contains only antibodies to the Lyme pathogen, then bands but no dot will appear on the membrane. Conversely, if the serum contains antibodies to *B. microti* but not the Lyme pathogen, then only the dot will appear on the membrane. Sera negative for antibodies to both pathogens will yield a negative Lyme Western blot and no dot.

Figure 1B:
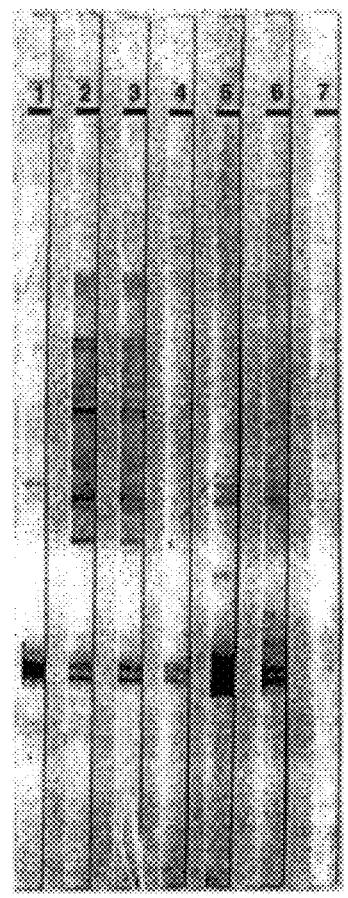
FIG. 1B provides the *Babesia microti* Western blot which confirms the preliminary screening dot-blot results shown in FIG. 1A.

In the case where a serum has been found positive for antibodies, for example, to *B. microti,* seropositivity may be confirmed by utilizing a Western blot assay for the *B. microti* antigen (FIG. 1B). A Western blot membrane is prepared with *B. microti* antigen following the same general procedure as used in preparation of Lyme Western blot membranes which are based on *B. burgdorferi* antigen. Accordingly, antigen is denatured and solubilized in sample buffer containing sodium dodecyl sulfate, Tris buffer and other components, and electrophoresed in a polyacrylamide gel following established procedures (Laemmli gel procedure). The resolved proteins are electrotransferred from the gel to a nitrocellulose membrane by established procedures (Towbin, H. et al., *PNAS* (*USA*) 76: 4350–4354 (1979)) and the membrane is saturated with non-specific protein (e.g., solubilized nonfat milk powder). The membrane can then be cut into individual strips for incubation with serum samples, or incubated in an Immunetics Miniblotter™ without cutting. Upon following the typical Western blot processing (e.g., steps 1–5 as above), bands appear on membranes which have been exposed to serum containing anti-Babesia antibodies. Several bands have been observed in sera from normal, healthy individuals, and these are not considered of diagnostic significance. A series of other bands correlate with seropositivity for *B. microti* as determined by other assays (i.e., immunofluorescence). Sera which generate any of these bands on the Babesia Western blot are defined as positive for antibodies to *B. microti.* The value of the Western blot assay as a confirmatory test for *B. microti* infection is the same as in the case of HIV and Lyme disease, the specificity of Western blot is higher than that of ELISA, immunofluorescence, or other screening tests. Thus, sera which appear indeterminate or positive by the dot test may be subsequently tested by Western blot assay. The combination of the dot screening test followed by the Western blot confirmatory test thus offers an effective means to detect and confirm the infection of a human patient.

While the method of the present invention is described in detail with respect to a *B. microti* antigen dot on the end of a Lyme western blot membrane, it will be appreciated that it is within the scope of the present invention that the modified membrane may be used for the detection of other tick-borne diseases. Antigen of other tick-borne diseases such as Human Granulocytic Ehrlichia (HGE), Human Monocytic Ehrlichia, Rocky Mountain Spotted Fever or tick-borne encephalitis, may also be applied to the Lyme Western blot membrane.

It will also be appreciated that the present invention may include screening for more than one disease in addition to the confirmatory test, e.g., a double dot blot, as well as screening for more than one disease without the confirmatory test. A combination of separate dots of tick-borne disease-specific antigens may thus be placed on the membrane. For example, separate dots of HGE and *B. microti* antigens on the end of a Lyme Western blot membrane would provide for screening of the two diseases most frequently co-transmitted by ticks along with Lyme disease. In addition, other combinations of antigens may also be used. For example, combinations of antigens for detecting various diseases may be chosen based on similarity of resulting disease symptoms, known antigenic cross-reactivity or other criteria. As an example, Lyme Western blot membranes have been prepared with separate dots of *B. microti* antigen and *Helicobacter pylori* antigen. Antibodies to *H. pylori* have been shown to occasionally cross-react with Lyme antigens on Lyme Western blots, suggesting the need to detect such spurious results in order to accurately interpret the Lyme Western blot.

Likewise, it is within the scope of the present invention that in place of dots of antigen, dots of antibody may be incorporated into the Western blot membrane. As an example, a purified goat anti-human IgG antibody can be applied to the membrane. When the membrane is processed through the usual Western blot incubation steps with human serum, the anti-human antibody will bind to IgG in the applied serum sample. IgG bound to the dot will then be detected by the enzyme conjugate, and will be revealed as a colored dot simultaneously with the Western blot bands.

Such an antibody dot can serve as an indicator that the serum sample tested did, in fact contain IgG in quantities sufficient to be detected in the Western blot assay. In the event of a negative Western blot result, the appearance of such a dot serves as verification that the assay procedure functioned properly. Other types of antibody dots can also be used to serve other needs, such as, for example, detection of subclasses of antibody in the sample.

It will be appreciated that the dots and bands of the Western blot membranes of the present invention may also be applied in other geometric shapes, such as lines, squares, etc. Pipets, syringes, inkjet devices and laser printing devices may be used to apply biological materials to the membranes.

The results of a combined dot blot—Western blot assay and confirmatory Western blot assay of the present invention may be read manually or by an automated device. For example, an instrument may be used which can scan a Western blot membrane which includes antigen dots on the end. The intensities of dots as well as Western blot bands can be measured electronically, and intensity values used in an appropriate algorithm to determine the significance of results. Such an instrument approach has the potential to be less subjective than evaluation of results manually, i.e., by eye.

The present invention also provides kits comprising a membrane of the present invention. The kits may also comprise reagents as well as apparatus for performing the methods described herein. The kit may further comprise instructions for use as well as appropriate packaging.

The following Specific Examples illustrate practice of the invention. These examples are for illustrative purposes only and are not intended in any way to limit the scope of the claimed invention.

SPECIFIC EXAMPLE 1

Results

The modified Western blot membrane of the present invention was used to evaluate sera. The membrane contained both a Western blot for Lyme disease as well as a dot-blot for babesiosis. Serum samples were treated in the same manner as in a conventional Lyme Western Blot assay: 1) incubation of the membrane with diluted serum; 2) buffer wash to remove unbound antibody; 3) incubation with enzyme-conjugated anti-immunoglobulin IgG or IgM; 4) buffer wash to remove unbound enzyme conjugate; and 5) incubation with enzyme substrate.

Immunoreactive bands are identified by comparing their positions with those of bands on the reference. A series of 10 antigen bands appear immunoreactive with sera from patients infected with *B. burgdorferi*. These bands are presently identified by apparent molecular weight in SDS-PAGE, although such molecular weights can only be considered approximate.

Positive Result: Appearance of any 5 of the 10 bands, including:

p93, p66, p58, p45, p41, p39, p30, p28, p23, p21

Negative Result: No bands present; appearance of any other band.

Six Babesia-positive sera were obtained from the CDC (Diagnostic Reference Laboratory) and yielded visible reactions with the Babesia antigen dot, while a Lyme-positive, Babesia-negative serum was non-reactive. To evaluate specificity, sixty-three sera samples obtained from blood donors at a Boston hospital were also tested. Donors were questioned with respect to history of tick bites to eliminate any undiagnosed cases of Lyme disease or babesiosis. Results yielded one weakly reactive specimen, indicating an apparent specificity greater than 98% in this population. In a previous study of blood donors at a Boston hospital, a background seropositivity rate for Babesia antibodies of 4.7% was reported. Popovsky, et al., *Transfusion* 28: 59–61 (1988).

Materials and Methods

The testing procedure was as follows. Wash buffer was prepared as phosphate-buffered saline containing 0.05% Tween-20. Sample dilution buffer was prepared by adding 5% dry milk to the Wash buffer. Conjugate dilution buffer was prepared as phosphate-buffered saline containing 0.05% Tween-20, 1% Polyvinylpyrrolidone, 1% dry milk, and 0.005% Thimerosal. Conjugate was affinity-purified goat anti-human IgG-alkaline phosphate. Substrate was a BCIP/NBT solution (5-bromo-4-chloro-3-indolyl phosphate/nitroblue tetrazolium, obtained from Kierkegaard & Perry, Gaithersburg, Md.).

To prepare for the assay, human serum samples, including a positive control, were diluted 100-fold in Sample Dilution Buffer. Lyme Western blot strips containing antigen for an additional tick-borne disease and Control band were transferred to the channels of a disposable plastic multichannel incubation tray and wetted with 1 ml each of Wash Buffer. Strips were then incubated with diluted serum samples for 30 minutes, after which samples were aspirated and replaced with wash buffer. Three washes were performed by rocking the incubation tray for three minutes on the rocker platform, then aspirating the wash buffer and repeating with fresh wash buffer. Strips were then incubated for 15 minutes with a 2,500-fold dilution of the conjugate in conjugate dilution buffer. After three more washes with wash buffer, strips were rinsed with distilled water and incubated with substrate. Bands were permitted to develop until all bands on the positive control strip were clearly visible. Strips were then rinsed thoroughly in distilled water and air dried.

The following describes a preferred method of the present invention. Dispense 1 ml of Wash Buffer into each channel of the incubation tray. Using forceps, place one immunostrip face up into each channel of the tray. Each strip should be marked at the top of the upper side with a number above a black line. Place the tray on the rocking platform and incubate for 1 min. to thoroughly wet the strips. All incubations on the rocking platform are performed at the speed of 10–15 cycles/min. Aspirate the liquid completely from individual channels using a disposable pipet tip connected to a vacuum system (a water aspirator with a trap is sufficient). Tilting the tray to empty channels should be avoided, as this could cause liquid to cross over and mix with adjacent samples during the following steps. Load samples to be tested immediately, in order to avoid drying of immunostrips. Include Positive and Negative Controls in each assay run. Pipet 1.0 ml of diluted IgG Negative Control Serum and 1.0 ml of diluted IgG Positive Control Serum into separate incubation channels. Pipet 1.0 ml of diluted serum sample into the appropriate numbered channel corresponding to the sample sequence in the protocol. Incubate on the rocking platform for 30 min. Aspirate liquid from each channel by vacuum as described above.

Rinse immunostrips three times by adding approximately 1 ml Wash Buffer to each channel, rocking 3 min., then aspirating the liquid by vacuum. To avoid cross-contamination, be careful not to overfill the channels.

Alternatively, use an eight-channel Immunowash (Immunetics LD-0512S, Nunc or equivalent). This will also speed up the procedure. Load 1.0 ml of diluted Enzyme Conjugate into each channel and incubate on the rocking platform for 15 min. Aspirate the conjugate and rinse strips once with Wash Buffer as described above.

Rinse strips twice with 1.0 ml of deionized water per channel and incubate on the rocking platform for 3 min. each rinse. Aspirate all liquid from the channels. Add 1.0 ml of Enzyme Substrate Solution to each channel (a multichannel pipettor is suggested for this step to start the enzymatic reaction at the same time in all channels). Place the tray on the rocking platform to initiate color reaction. Allow the color reaction to develop until the positive control serum immunoreactive bands are clearly visible, usually 6–7 min. Do not incubate longer than 10 min. Stop color development by aspirating substrate from tray and rinsing the immunostrips immediately with two brief changes of distilled or deionized water. Using forceps, transfer immunostrips face up to a paper towel and let air dry. Do not dry immunostrips between paper towels or pat dry and don't attempt to interpret results until blot is completely dry.

For improved results, note the following: deviations from the protocol may lead to a loss of sensitivity or false interpretations; mix reagents well when diluting before use to obtain homogeneous solutions; diluted reagents must be used within 24 hours, with exception of buffers; use high-grade distilled or deionized water for preparation of buffers; use a rocker platform for agitation, not a horizontal shaker; and, use separate pipette tips for each sample or reagent to avoid cross contamination.

SPECIFIC EXAMPLE 2

A confirmatory Western blot assay was used to confirm the presence of antibodies to *B. microti*. Generally, the Western blot assay procedures described above and known to those skilled in the art were employed. Proteins from *B. microti* were resolved by electrophoresis and transferred by electroblotting onto a nitrocellulose membrane. The antigen bearing membrane was cut into strips for testing individual samples. Sera were incubated with the strips at 100X dilution.

If present in the serum, anti-Babesia antibodies will bind to antigens on the immunostrip. After incubation, unbound material is washed away and each immunostrip is incubated with an alkaline phosphatase-conjugated anti-human IgG serum. After a second wash, the conjugate bound to human IgG/Babesia antigen complexes is visualized by exposing the enzyme to its substrate plus a chromogen which precipitates as a dark purple colored band. The enzyme-substrate reaction is stopped by rinsing the immunostrips with distilled water. Visualization of specific protein bands indicates the presence in the serum of IgG antibodies directed against Babesia antigens.

U.S. Ser. No. 08/928,155, filed Sep. 12, 1997, entitled "Western Blot And Method For Detecting Babesia" further describes the Babesia Western blot and method and is herein expressly incorporated by reference.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification and following claims.

All patents, patent applications and other publications cited herein are expressly incorporated by reference.

What is claimed is:

1. A method for detecting Lyme disease and at least one additional tick-borne disease in a sample comprising the steps of:
    a) applying the sample to a Western blot membrane comprising a Lyme disease antigen and a dot-blot antigen for the additional tick-borne disease; and
    b) simultaneously detecting binding of the Lyme disease antigen with antibody in the sample and
    binding of antigen for the additional tick-borne disease with antibody in the sample.

2. The method of claim 1, wherein the membrane is a nitrocellulose membrane.

3. The method of claim 1, wherein the sample is human serum.

4. The method of claim 1, wherein the additional tick-borne disease is babesiosis.

5. The method of claim 1, wherein the additional tick-borne disease is ehrlichiosis.

6. The method of claim 1, wherein the membrane further comprises a control band of antibody which when binds to antibody in the sample serves as an indicator showing whether the sample contains antibody in sufficient quantity to be detected.

7. The method of claim 1, further comprising the step of confirming the presence of antibody against antigen for the additional tick-borne disease in the sample by Western blot assay.

8. The method of claim 4, further comprising the step of confirming the presence of antibody against antigen for the additional tick-borne disease in the sample by Western blot assay.

9. The method of claim 5, further comprising the step of confirming the presence of antibody against antigen for the additional tick-borne disease in the sample by Western blot assay.

10. A Western blot membrane comprising Lyme disease antigen and a dot-blot antigen for an additional tick-borne disease.

11. A Western blot membrane of claim 10, wherein the additional tick-borne disease is babesiosis.

12. A Western blot membrane of claim 10, wherein the additional tick-borne disease is ehrlichiosis.

13. The Western blot membrane of claim 10, wherein the membrane further comprises a control band of antibody which when binds to antibody in the sample serves as an indicator showing whether the sample contains antibody in sufficient quantity to be detected.

14. A diagnostic kit comprising a modified Western blot membrane comprising Lyme disease antigen and antigen for an additional tick-borne disease.

15. The diagnostic kit of claim 14, wherein the additional tick-borne disease is babesiosis.

16. The diagnostic kit of claim 14, wherein the additional tick-borne disease is ehrlichiosis.

* * * * *